United States Patent [19]

Itoi et al.

[11] 4,063,816

[45] Dec. 20, 1977

[54] CHEMICAL REACTION VELOCITY MEASURING APPARATUS

[75] Inventors: Nobuo Itoi, Zushi; Teruo Shimamura, Yokosuka; Yoshio Fukami, Yokohama; Hidetoshi Mori, Kawasaki; Kenji Miwa, Chigasaki, all of Japan

[73] Assignee: Nippon Kogaku K.K., Tokyo, Japan

[21] Appl. No.: 641,264

[22] Filed: Dec. 16, 1975

[30] Foreign Application Priority Data

Mar. 3, 1975 Japan ............................ 50-24976

[51] Int. Cl.² .......................... G01J 3/42; G01J 3/46; G01N 21/22
[52] U.S. Cl. .................................. 356/93; 23/230 R; 23/253 R; 356/180; 356/188; 356/195; 356/205
[58] Field of Search ...................... 356/88, 93, 95, 96, 356/180, 184, 188, 195, 201, 205, 206; 23/230 R, 230 B, 253 R

[56] References Cited

U.S. PATENT DOCUMENTS

| | | | |
|---|---|---|---|
| 3,523,737 | 8/1970 | Wood et al. ........................ | 356/180 |
| 3,748,044 | 7/1973 | Liston ................................ | 356/180 |
| 3,790,279 | 2/1974 | Skala ................................. | 356/205 |
| 3,811,780 | 5/1974 | Liston ................................ | 356/180 |
| 3,847,486 | 11/1974 | McCabe ............................. | 356/96 |
| 3,901,600 | 8/1975 | Johnson, Jr. et al. ............... | 356/88 |
| 3,915,644 | 10/1975 | Walraven ........................... | 23/253 R |
| 3,963,909 | 6/1976 | Atwood et al. .................... | 23/230 R |

Primary Examiner—Vincent P. McGraw
Attorney, Agent, or Firm—Fitzpatrick, Cella, Harper & Scinto

[57] ABSTRACT

A chemical reaction velocity measuring apparatus by detecting change in light absorbance.

The apparatus includes an optical system containing a means for alternately passing the lights of at least two different wavelengths and a detector;
  a sample holding means for arranging plural samples at regular spacings;
  an advancing means for intermittent advancement of said samples in such a manner that a sample and a vacant spacing between samples are alternately positioned at said two colorimetric measuring devices; and
  a means for detecting the change of light absorbance from the difference of absorbances measured at two wavelengths by said two colorimetric measuring devices.

10 Claims, 17 Drawing Figures

CHEMICAL REACTION VELOCITY MEASURING APPARATUS

BACKGROUND OF THE INVENTION

1. Field of the Invention

The present invention relates to a reaction velocity measuring apparatus for rapid and accurate measurement of the velocity of chemical reactions.

2. Description of the Prior Art

The principle of the measurement of velocity of chemical reaction is explained in the following with particular reference, as an example, to an enzymatic reaction.

It is already known to determine the amount of enzyme indirectly from the reaction velocity per unit time or enzyme activity by measuring the reaction velocity of a reaction catalyzed by said enzyme. Under certain conditions, i.e. under suitable temperature conditions (under 30° C, for example) with a suitably low enzyme concentration and a suitably high substrate concentration, each molecule of enzyme independently reacts with the substrate with a velocity proportional to the concentration of enzyme. In case the reaction velocity is proportional to the amount of enzyme and does not depend on time, the enzymatic reaction proceeds at a constant velocity. Stated differently the amount of reaction product stands in a linear relationship with time, signifying that the light absorption coefficient becomes proportional to time.

The measurement of the reaction velocity of enzyme is usually achieved by measuring the difference of light absorbance in one minute while such proportional relationship stands, and the IU, i.e. the amount of enzyme per one liter is defined by the following equation:

$$IU = \Delta A \cdot K$$

wherein $\Delta A$ represents the difference of light absorbance in one minute, and $K$ is a constant (hereinafter referred to as $K$ factor).

In the prior art the velocity of an enzymatic reaction is measured by recording the light absorbance on a recorder, reading the difference of light absorbance in one minute within a range where such linear relationship is visually observable and multiplying said difference by said $K$ factor manually or by measuring light absorbance at suitable time intervals, electrically subtracting and converting thus obtained values to obtain the difference in one minute, and multiplying said difference by said $K$ factor.

In case of determining the enzyme activity from the change of light absorbance in the course of a reaction, the period required for such determination is represented by (number of samples) × (time of measurement necessary for one sample). On the other hand the colorimetry method wherein the reaction velocity is calculated from the light absorbance in the chemical equilibrium state after the completion of chemical reaction requires a period represented by (time necessary for reaction) + (number of samples) × (period of measurement necessary for one sample) since in this case plural samples are simultaneously subjected to reaction and then to measurements after the completion of reaction. The former requires a shorter time and is therefore advantageous if the number of samples is limited, but takes several times longer period in comparison with the latter which requires only several seconds for the measurement of each sample, if a considerably large number of samples is to be measured. With respect to the accuracy of measurement, however, the latter is inferior since the measurement is realized in a range where the light absorbance is not linearly correlated with the reaction velocity. For this reason the former method is more adequate for a more accurate measurement of the enzyme activity. With further respect to the former method, the usually employed way with electric subtraction is realized by the measurement of light absorbance A at time $t_1$ followed by that of light absorbance A' at time $t_2$ to determine a ratio $(A_2 - A_1)/(t_2 - t_1)$.

In this manner the measuring apparatus is not in operation between two measurements at $t_1$ and $t_2$, and has therefore considerable idle time. It has therefore been proposed to utilize such idle time between $t_1$ and $t_2$ for the measurements of other samples thereby improving the efficiency of apparatus and increasing the number of treated samples. In this case the sample measured at time $t_1$ has to be returned to the original position at $t_2$ since a sample has to be subjected to two measurements. For this purpose there have been proposed devices in which plural samples are arranged in a reciprocating rack or arranged in circular positions. However such devices are inadvantageous as the number of samples accomodated is inevitably limited. More specifically the devices of this kind become inevitably large in dimensions, if the number of samples is increased, and require complicated electric circuitry as the memory circuits explained later are required in same number as the samples. Thus, there have to be frequent interruptions of operations for the replacement of measured samples with unmeasured ones.

Furthermore, because two measurements are effected with time interval $t_1$ - $t_2$, there would be variation in the optical source or drifts of electrical portions such as amplifier, which adversely effects measurement accuracy. It is better to adopt double beam method for eliminating such drawback, which method can eliminate such influence caused by fluctuation in the light source or by a back ground condition which is constant between times $t_1$ - $t_2$ as contamination of the sample cell for measuring the difference of absorbance. However, it is impossible to eliminate an undesirable influence caused by back ground such as bubbles in the cell, which varies between the period $t_1$ - $t_2$. For effecting such elimination it is necessary to adopt spectrophotometry at two wavelengths, which enables to eliminate back grounds at time $t_1$ and time $t_2$ respectively so that measurements can be made with accuracy even if there occur any variations in back grounds between the time period $t_1$ - $t_2$.

In the following there is given a detailed description on the measurement of reaction velocity by spectrophotometry at two wavelengths.

The absorbances $A_1$ and $A_2$ at wavelengths $\lambda_1$ and $\lambda_2$ of a sample at a time $t_1$ can be expressed by the following equations:

$$A_1 = \log \frac{I\lambda_{10}(t_1)}{I\lambda_1(t_1)} = K_1 cx + b_1 \quad (1)$$

$$A_2 = \log \frac{I\lambda_{20}(t_1)}{I\lambda_2(t_1)} = K_2 cx + b_2 \quad (2)$$

wherein $I\lambda_{10}(t_1)$: incident light of wavelength $\lambda_1$
$I\lambda_{20}(t_1)$: incident light of wavelength $\lambda_2$
$I\lambda_1(t_1)$: transmitted light of wavelength $\lambda_1$ $I\lambda_2(t_1)$: transmitted light of wavelength $\lambda_2$
$K_1$: absorption coefficient at $\lambda_1$
$K_2$: absorption coefficient at $\lambda_2$
$c$: sample concentration
$x$: light path length
$b_1, b_2$: back grounds at $\lambda_1, \lambda_2$.

It can be assumed that $b_1 = b_2$ if the wavelengths $\lambda_1$ and $\lambda_2$ are selected mutually close.

Similarly following equations stand at a time $t_2$:

$$A_1' = \log \frac{I\lambda_{10}(t_2)}{I\lambda_1(t_2)} = K_1(c + \Delta c)x + b_1' \quad (3)$$

$$A_2' = \log \frac{I\lambda_{20}(t_2)}{I\lambda_2(t_2)} = K_2(c + \Delta c)x + b_2' \quad (4)$$

The difference of absorbances at $\lambda_1$ and $\lambda_2$ at time $t_1$ is obtained as follows:

$$\Delta A(t_1) = A_1 - A_2 = \log \frac{I\lambda_{10}(t_1)}{I\lambda_1(t_1)} \cdot \frac{I\lambda_2(t_1)}{I\lambda_{20}(t_1)} \quad (5)$$
$$= (K_1 - K_2) cx$$

Similarly the difference of absorbance $\Delta A (t_2)$ at time $t_2$ is:

$$\Delta A(t_2) = A_1' - A_2' = \log \frac{I\lambda_{10}(t_2)}{I\lambda_1(t_2)} \cdot \frac{I\lambda_2(t_2)}{I\lambda_{20}(t_2)} \quad (6)$$
$$= (K_1 - K_2)(c + \Delta c)x$$

If the fluctuation of light source is small between times $t_1$ and $t_2$, there stands:

$$\frac{I\lambda_{10}(t_1)}{I\lambda_{20}(t_1)} = \frac{I\lambda_{10}(t_2)}{I\lambda_{20}(t_2)}.$$

Thus the difference of absorbances at $t_1$ and $t_2$ can be expressed as follows:

$$\Delta A(t_2) - \Delta A(t_1) = \log \frac{I\lambda_2(t_2)}{I\lambda_1(t_2)} - \log \frac{I\lambda_2(t_1)}{I\lambda_1(t_1)} \quad (7)$$
$$= (K_2 - K_1) \Delta c \cdot x$$

and is therefore proportional to the change $\Delta c$ of concentration of the sample between times $t_1$ and $t_2$. Thus, by multiplying a factor $K' = k \cdot [K_1/(K_2 - K_1)]$, the amount IU of the enzyme is represented as follows:

$$IU = K' \{\Delta A(t_2) - \Delta A(t_1)\} \quad (8)$$
$$= K \cdot K_1 \cdot \Delta c \cdot x$$
$$= K \cdot \Delta A$$

In the spectrophotometric method with two wavelengths it is necessary to use a same optical system for the measurements at $t_1$ and $t_2$ since there will be a difference in wavelength characteristics if different optical systems are employed.

SUMMARY OF THE INVENTION

The first object thereof is to provide an apparatus 1. which can measure the velocity of chemical reaction capable, without the above-mentioned drawbacks, of utilizing the above-mentioned idle time between $t_1$ and $t_2$ for the measurements of other samples, thereby improving the efficiency of apparatus and increasing the number of treated samples;

2. which can measure the velocity of chemical reaction which is freed from the undesirable effect on the measured values resulting from eventual drifts in the electrical systems such as light source, detector, amplifier etc. in the time period from $t_1$ to $t_2$ in order to effect the measurements at $t_1$ and $t_2$ under as same conditions as possible and to ensure an as high accuracy as possible; and 3. which can measure the velocity of chemical reaction which is freed from the undesirable effect on the measured values resulting from the eventual fluctuation of background in the time period from $t_1$ to $t_2$ for example by eventual formation of bubbles therein in the sample cell by means of eliminating the background component at $t_1$ and $t_2$.

Figure 10:
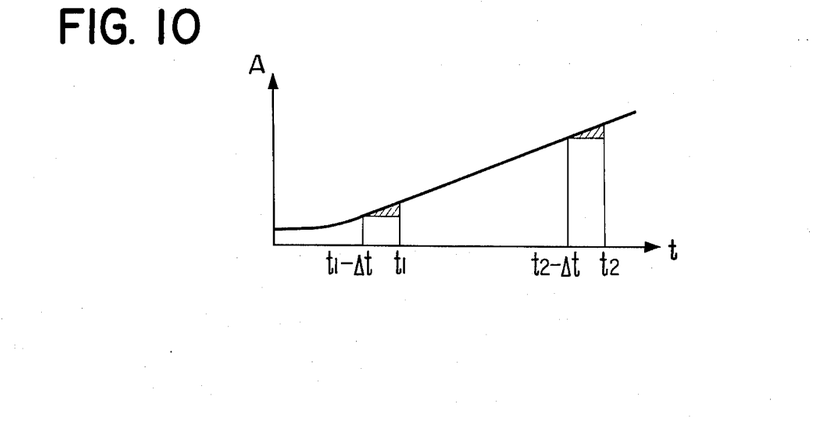
FIG. 10 is a drawing showing the relation between absorbance of sample and time.

Further, in case of an enzymatic reaction it is to be noted that the reaction is initiated by a non-linear so-called lag phase, and takes certain time lag before it reaches the linear portion (as shown in FIG. 10 indicating the light absorption A in ordinate against the time in abscissa) where the measurements are to be effected for accurate determination of enzyme activity.

The second object of the present invention, therefore, is to provide an apparatus for measuring the velocity of chemical reaction which is added, to the apparatus achieving the aforementioned first object, with a linearity monitor capable of judging whether the measurements are effected in such linear portion and indicating the result of such judgment.

The present invention will be further clarified by the following description with specific reference to the embodiments thereof shown in the attached drawings, wherein the like parts and elements are designated by like numerals and symbols throughout therein.

Figure 3:
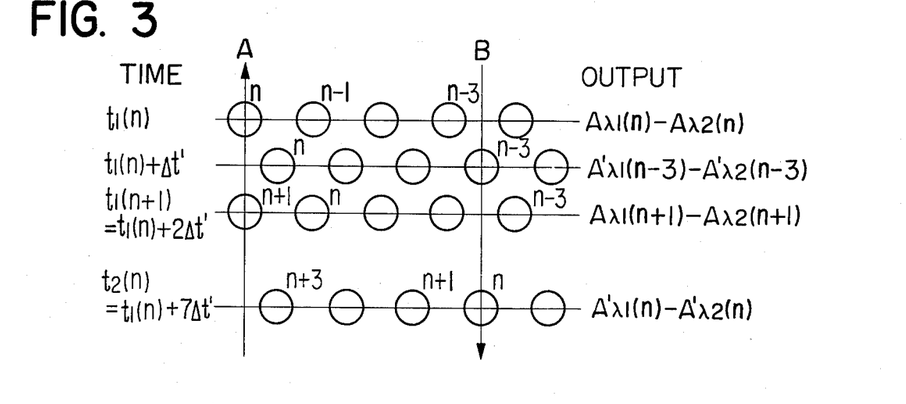
FIG. 3 is a pulse chart for explaining the advancement of the sample cell of the first embodiment.

In the following explained is a first embodiment of the present invention achieving the aforementioned first object thereof with reference to FIGS. 1 - 3.

DESCRIPTION OF THE PREFERRED EMBODIMENTS

In the following there is given a first explanation on a first embodiment for achieving the first object of the present invention. Referring to FIG. 1, 1 is a light source, 2 is a convex lens for converting the light from the light source 1 into a parallel beam, 3 is a filter chopper provided with two interference filters $F_1$ and $F_2$ for alternately selecting two determined wavelengths, of a shape shown in FIG. 2, in which the interference filters $F_1$ and $F_2$ respectively select the wavelengths $\lambda_1$ and $\lambda_2$, 4 is a convex lens for focusing said parallel light beam to the central position of reaction cuvettes 13, 5 is a convex lens for converting thus focused light beam into a parallel beam, 6 and 7 are planar mirrors for converting the direction of said parallel light beam, 8 is a convex lens for focusing the light beam in the similar manner as the lens 4, and 9 and 10 are convex lenses for introducing said light beam into a detector 11, such as a photomultiplier, for converting the light signal from the lens 4 into an electric signal. 12 are sample cells for holding samples, and 13 are mutually connected cell holders for holding the sample cells. The cell holders 13 are provided with recesses 13'. A sample holding means is thus composed of the sample cells 12, cell holders 13 and recesses 13'. 14 is a cam engaged with said recesses 13' provided on the cell holders and rotated by a motor 14' to intermittently advance the cell holders. The cam 14 and motor 14' compose an advancing means.

Figure 5:
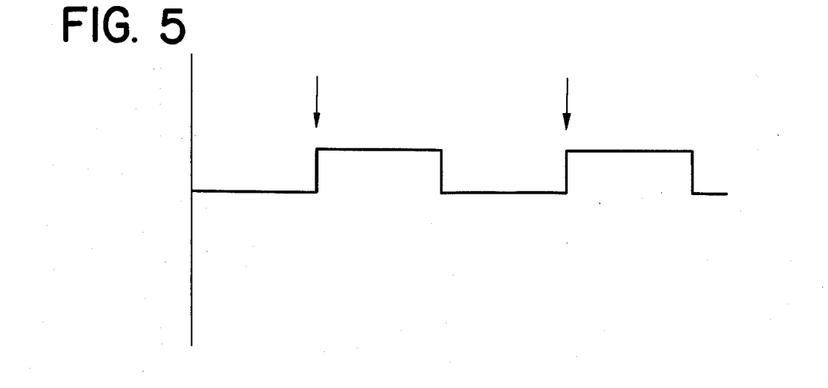
FIG. 5 is an output pulse chart generated from a synchronous pulse generating circuit used in the second embodiment.

The two light beams crossing the cell holders 13 are respectively referred to as the light beam A and beam B. The intermittent advancement of the sample cells 12 and cell holders 13 by means of recesses 13' and cam 14 is realized in such a way that a cell 12 is positioned at the beam A at time $t_1$ and another cell 12 is positioned at the light beam B at time $t_1 + \Delta t'$ as will be explained in detail in connection with FIG. 3. As shown in FIG. 3, the n-th sample is positioned in the light beam A for measurement at time $t_1(n)$, while there is no sample cell positioned in the light beam B. In this state the difference of absorbances at two wavelengths, $A\lambda_1(n) - A\lambda_2(n)$, of the n-th sample at time $t_1(n)$ is measured. At time $t_1(n) + \Delta t'$, there will be the $(n-3)$-th sample positioned in the beam B whereas there is no sample in the beam A to allow the measurement of $A'\lambda_1(n-3) - A'\lambda_2(n-3)$. At time $t_2(n) = t_1(n) + 7\Delta t'$ after repeated advancements in this manner at each $\Delta t'$, the n-th sample is located in the light beam B to effect the measurement of $A'\lambda_1(n) - A'\lambda_2(n)$. The revolution of motor 14' is so selected that $7\Delta t'$ is equal to one minute. 15 is an amplifier for amplifying the electric signal from the detector 11, and 16 is a synchronized rectifying circuit functioning in synchronization with the signal of two wavelengths $\lambda_1$ and $\lambda_2$. Further, 16' is a synchronizing pulse generator for generating pulses for driving the synchronized rectifying circuit 16 in synchronization with the filter chopper 3. 17 and 17' are logarithmic converters for converting the signals separated by the synchronized rectifying circuit 16 into the absorbance signals, which respectively receive the signals of wavelength $\lambda_1$ and that of wavelength $\lambda_2$. 18 is subtractor for subtracting the output of the logarithmic converter 17 from the output of the logarithmic converter 17'. 19 is an analog-digital converter for converting the analog electric signal from the subtractor 18 into digital signals. 20 is a switch provided with contacts X and Y which are closed respectively when there is a sample in the light beam A or in the beam B. The switching of said contacts is controlled by a synchronizing pulse generating circuit 20' generating the pulses shown in FIG. 5, in such a way that the contact X or Y is closed respectively when the circuit 20' releases a high or low level output signal. In FIG. 5, each arrow shown the completion of the advancement of the sample. 21 is a memory circuit receiving input signals from the contact X of the switch 20 for successively memorizing the signals therefrom. The memory circuit 21 is composed of a four-unit shift register which memorizes the signal of for example n-th sample in the first memory element upon receipt of such signal. Upon receipt of the signal of the $(n+1)$-th sample after a period $2\Delta t'$, the content of the first memory element is shifted to the second memory element while said received signal is memorized in the first memory element. In this manner, upon receipt of the signal of the $(n+3)$-th sample, the signal of the n-th sample is memorized in the fourth memory element. 22 is a subtractor provided with a minuend input terminal and a subtrahend input terminal which respectively receive the output of the contact Y of switch 20 and the output of fourth memory element of the memory circuit 21. 23 is a multiplier for multiplying the output of the subtractor 22 by the value K given by the equation (8) thereby converting the absorbance signal into the international unit amount of enzyme. 24 is a printer for printing the output of the multiplier 23.

Figures 1, 2:
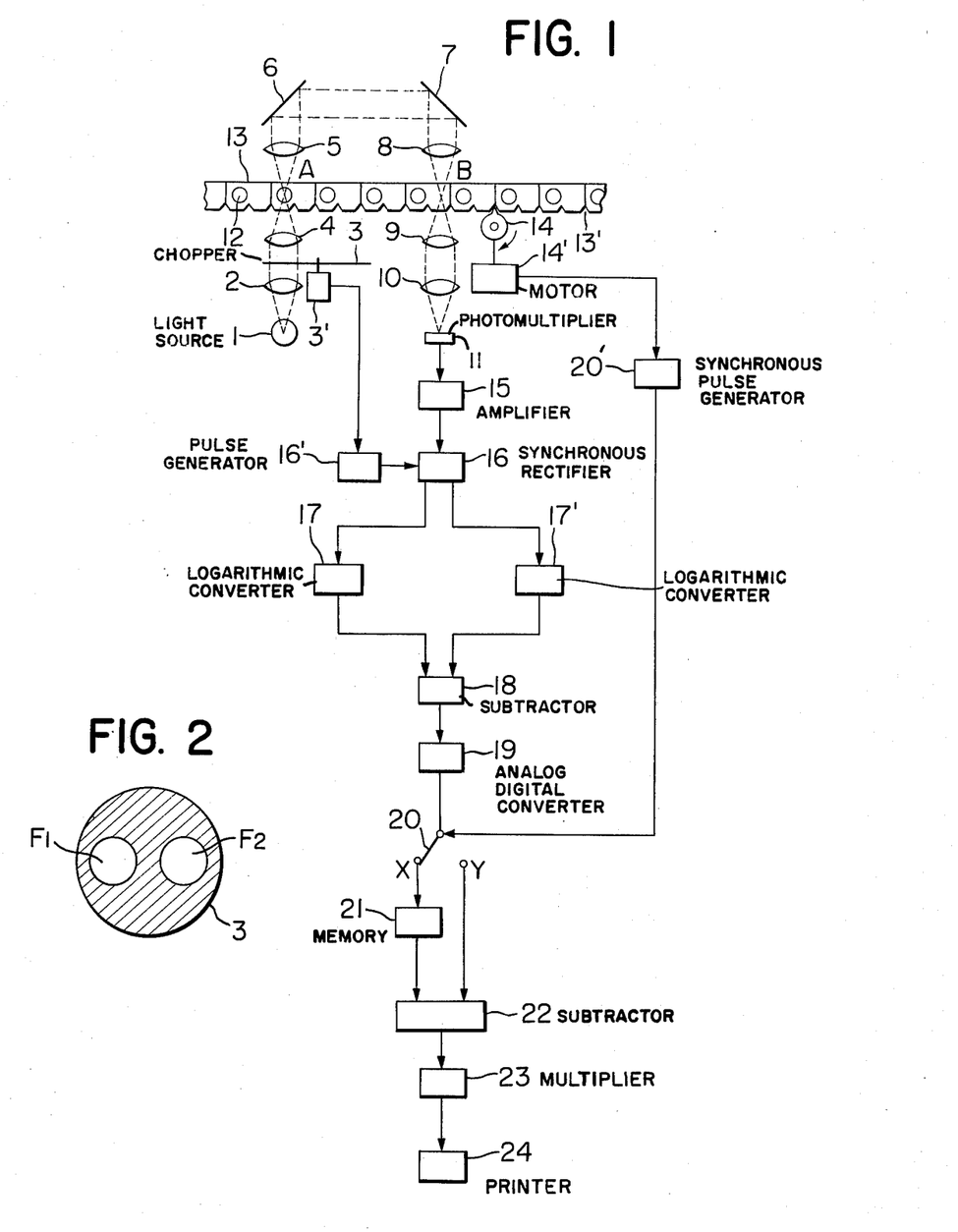
FIG. 1 is a drawing showing a first embodiment of the present invention.
FIG. 2 is a drawing showing the chopper employed in the first embodiment.

In the present embodiment of the composition explained above, a sample cell 12, when located in the light beam A as shown in FIG. 1, is alternately irradiated by the lights $I\lambda_{10}(t_1)$ and $I\lambda_{20}(t_1)$, and the signals $I\lambda_1(t_2)$ and $I\lambda_2(t_2)$ detected by the detector 11 are amplified, then subjected to synchronized rectifying and to logarithmic conversion. The signals of $\lambda_1$ and $\lambda_2$ converted into absorbance signals are supplied to the subtractor 18 to determine the log $(I\lambda_2(t_1)/I\lambda_1(t_1))$ in the foregoing equation (7), which is further converted into a digital signal by 19 and is memorized, through the contact X of switch 20, in the memory circuit 21. Successively the measurements are repeated on other samples, and the sample having crossed the light beam A reaches the beam B one minute after such crossing. Thus the contact Y of switch 20 is closed, and the subtractor 18 determines the value log $(I\lambda_2(t_2)/I\lambda_1(t_2))$ in the equation (7) which is supplied to the subtractor 22. In this manner $\Delta A(t_1) - \Delta A(t_2)$ in the equation (7) is obtained as the n-th memory element of the memory circuit 21 memorized the absorbance signal of the first sample at time $t_1$. Thus obtained value is multiplied by K in the equation (8) in the multiplier 23 and is printed digitally by the printer 24.

Figure 4:
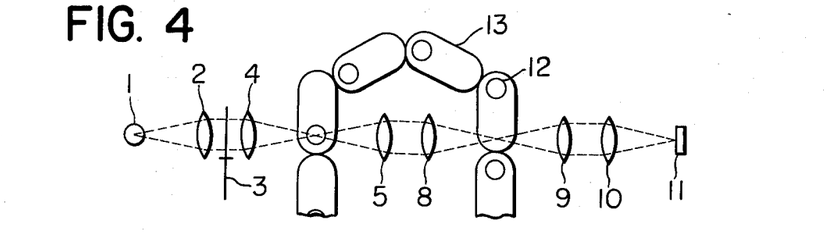
FIG. 4 is a drawing showing a modification of the first embodiment.

In the present first embodiment the samples are advanced linearly while the optical system is deflected by the mirrors 6 and 7 in order to effect the measurements at times $t_1$ and $t_2$ with a same optical system, but the same purpose can be realized by deflecting the advancing path of the cell holders 13 combined with a linear optical system as shown in FIG. 4.

In the following there is given a detailed explanation with particular reference to FIGS. 6 and 7 on a second embodiment for achieving the second object of the present invention. The second embodiment shown in FIGS. 6 and 7 is composed of the apparatus for measuring the reaction velocity as shown in the first embodiment of the present invention and a differential linearity monitor.

Figure 6:
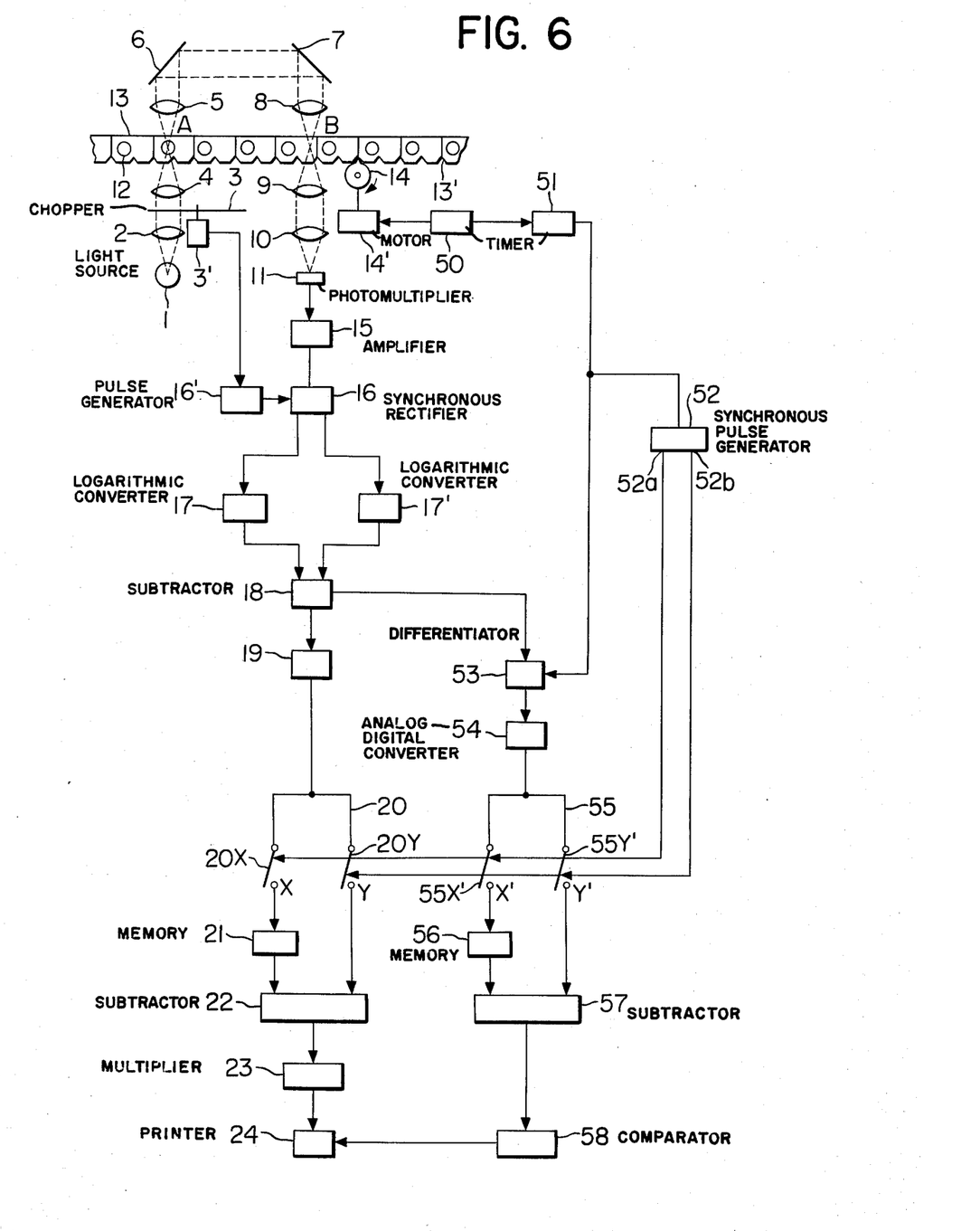
FIG. 6 is a drawing showing a second embodiment of the present invention.
Figure 7A:
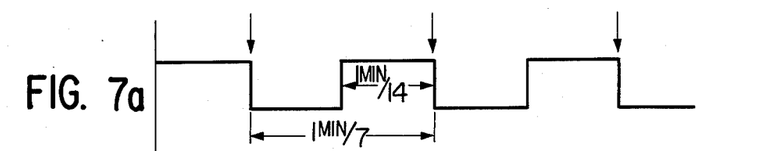
FIG. 7a–7d are pulse charts for explaining the function of principal portion of the second embodiment.
Figure 7B:
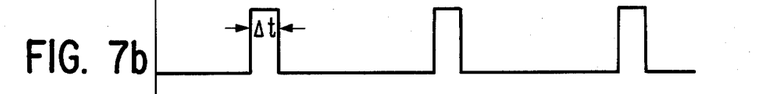
Figure 7C:
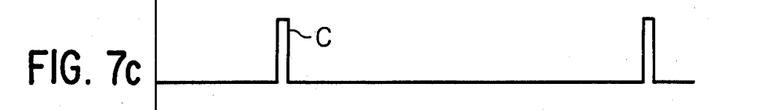
Figure 7D:
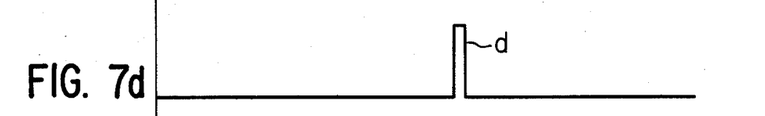

Referring to FIG. 6, 50 is a first timer generating pulses shown in FIG. 7a for driving the motor 14' which controls the cam 14 so as to advance the cell holders 13 at every 1/7 minute interval. In this manner a cell crossing the beam A reaches the beam B after one minute. The arrow in FIG. 7b indicates the completion of the advance of the sample cells. Further, 51 is a second timer which is put into function for a period $\Delta t$ at the termination as start of the output pulses of the first timer 50 to generate the pulses as shown in FIG. 7b. 52 is a synchronizing pulse generating circuit for generating the pulses c and d as shown in FIG. 7c and FIG. 7d in synchronization with the termination of pulses from the second timer 51, the pulses c and d being alternately released from the output terminals 52a and 52b, respectively. 55 is a switch provided with contacts X' and Y', and switching arms 55X' and 55Y'. 53 is a differentiating circuit for differentiating the absorbance signal from the subtractor 18 by time upon receipt of output pulses from the second timer 51. Further, 54 is an analog-digital converter. 56 is a memory circuit similar to the aforementioned memory circuit 21 but composed of a 10-unit shift register, of which output is connected to the minuend input terminal of a subtractor 57, of which subtrahend input terminal is connected to the contact Y'. 58 is a comparing circuit which compares the output of the subtractor 57 with a predetermined tolerance range $0 \pm \Delta V$ ($\Delta V$: noise signal etc.) and forwarding the output to the printer 24 when the output is located outside said tolerance range.

The contacts X, Y are closed only when the pulse c shown in FIG. 7c is supplied from the terminal 52a of the pulse generating circuit 52 to the switching arm 20X or 55X', respectively. Further the contact Y or Y' is closed only when the pulse d shown in FIG. 7d is supplied from the terminal 52b of the pulse generating circuit 52.

In the present embodiment of the above-explained composition, the difference between the absorbance at $t_1$ and that at $t_2$ which is one minute later, or the signal indicating the difference of absorbance in 1 minute is obtained from the subtractor 22, and simultaneously a signal indicating the difference of differentiated absorbances at $t_1$ and $t_2$ is obtained from the subtractor 57. The output signal from the subtractor 22 is multiplied by the K factor in the multiplier 23 and is printed by the printer 24, while the output signal of the subtractor 57 is compared with aforementioned tolerance range in the comparing circuit 58 and is forwarded to the printer 24 only when said signal is located outside said tolerance range. In this manner, simultaneously with the printing of signal of enzyme amount by the printer 24, the signal from the comparing circuit 58 is printed solely when the output signal of the subtractor 57 is located outside said tolerance range, i.e. when the measurements at $t_1$ and $t_2$ are made in the non-linear portion of reaction, thus enabling to recognize this fact. Such measurements are effected at every interval of 1/7 minute, and the results are printed by the printer 24.

In the following there is given a detailed explanation with reference to FIG. 8 on a third embodiment for achieving the third object of the present invention.

Figure 8:
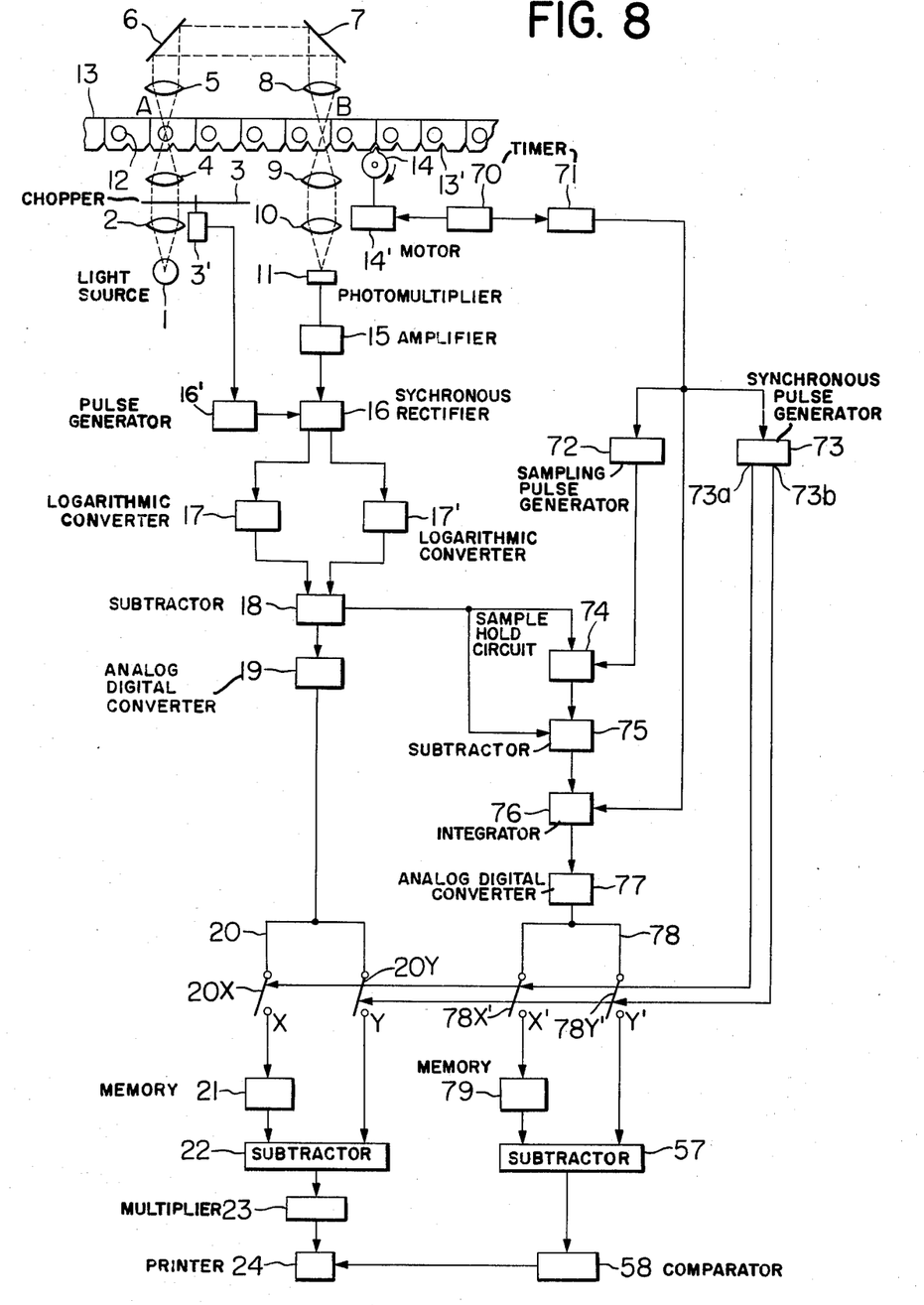
FIG. 8 is a drawing showing a third embodiment of the present invention.

The third embodiment of the present invention shown in FIG. 8 is composed of an apparatus for measuring reaction velocity of the first embodiment and an integrating linearity monitor.

In this embodiment, simultaneously with the measurement of the difference between the absorbances $A_1$ and $A_2$ at $t_1$ and $t_2$, the integrated values of the variation of absorbance at $t_1$ and $t_2$, or the hathced areas in FIG. 10:

$$\int_{t_1 - \Delta t}^{t_1} \Delta A_1 dt \text{ and } \int_{t_2 - \Delta t}^{t_2} \Delta A_2 \Delta t$$

are measured and mutually compared in order to evaluate whether the measurements are effected in the linear portion of the reaction.

Figure 9A:
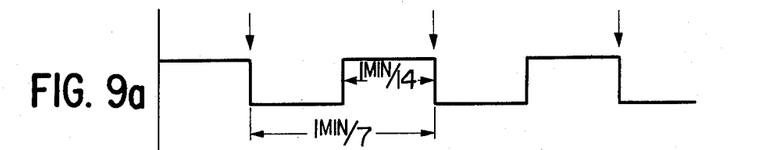
FIG. 9a–9e are pulse charts for explaining the function of principal portion of the third embodiment.
Figure 9B:
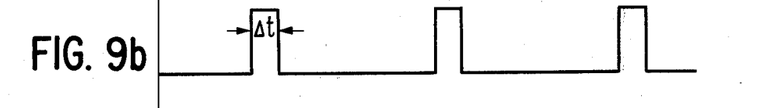
Figure 9C:
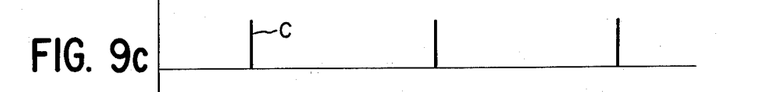
Figure 9D:
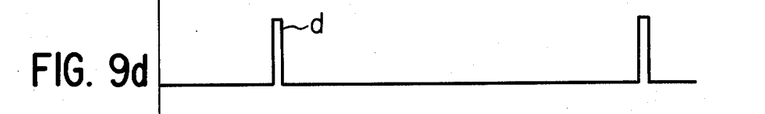
Figure 9E:
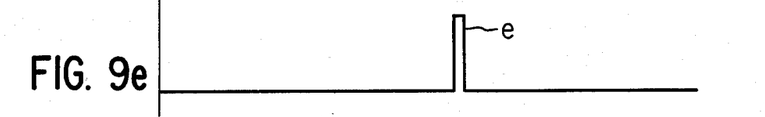

Referring to FIG. 8, 70 is a first timer for generating pulses as shown in FIG. 9a for driving a motor 14', which therefore controls a cam 14 to advance the cell holders 13 at every 1/7 minute interval. Thus the sample cells reach the light beam B one minute after crossing the light beam A. The arrow in FIG. 9 indicates the completion of advancement of sample cells. 71 is a timer similar to aforementioned second timer 51 for generating pulse signals as shown in FIG. 9b. 72 is a sampling pulse generating circuit for generating pulse signals as shown in FIG. 9c at the initiation of each pulse from said timer 71. 73 is a synchronizing pulse generating circuit similar to the aforementioned circuit 52 and is provided with terminal 73a and 73b for generating respectively the pulses d and e shown in FIGS. 9d and 9e. Switches 20 and 78 are controlled in such a manner that the switching arms 20X and 78'X thereof come in contact with the contacts X and X' upon receipt of said pulse d and the switching arms 20Y and 78'Y come into contact with the contacts Y and Y' thereof upon receipt of the pulse e. 74 is a sample hold circuit which is put into function for a determined period at least equal to $\Delta t$, upon receipt of the pulse c from the sampling pulse generating circuit 72, to hold the absorbance signal from the subtracting circuit 18 for said period and supply said signal to a subtracting circuit 75, which also receives, as the minuend, the absorbance signal from the subtracting circuit 18 to obtain the difference of said two input signals. 76 is an integrating circuit which is put into function upon receipt of the pulse shown in FIG. 9b from the timer 71 to integrate the absorbance signal from the subtracting circuit 75 for a period $\Delta t$. 77 is an analog-digital converter. 79 is a memory circuit similar to the circuit 21 and composed of a four unit shift register.

In the present embodiment of the composition explained above, the subtractor 57 generates a signal indicating the difference between the integration of the absorbance signal from $t_1 - \Delta t$ to $t_1$ and that from $t_2 - \Delta t$ to $t_2$ is one minute after $t_1$. Said difference signal is compared in the comparing circuit 58 with aforementioned tolerance range and forwarded to the printer 24 only if said difference signal is located outside said tolerance range. In this manner, simultaneous with the printing of the signal indicating the amount of enzyme by the printer 24, the signal from said comparing circuit 58 is also printed if the measurements at $t_1$ and $t_2$ are made in a non-linear portion of the reaction thereby enabling to recognize this fact. Such measurements are effected at every 1/7 minute interval, and the results are printed by the printer 24.

Although the foregoing explanation has been concentrated on the measurement of velocity of enzymatic reaction, the apparatus of the present invention is generally applicable effectively for the analysis of the phenomena wherein the absorbance of a given wavelength of reaction product, and particularly of the zero-order reactions. For example the redox reaction of thytochrome C can be measured by the detection of absorbance at 510 nm. Furthermore, it is naturally easily possible to design electric circuit for calculating the reaction velocity of first-order reactions from the absorbances at time $t_1$ and $t_2$.

We claim:

1. Apparatus for measuring the velocity of a chemical reaction by detecting the changes in light absorbance of samples in which said reaction is taking place, said apparatus comprising:

a. means for generating a first light beam of a wavelength ($\lambda_1$) and a second light beam of a wavelength ($\lambda_2$) alternately;

b. means for holding said samples in a line so that the samples are spaced by a predetermined distance;

c. means for directing said two light beams along one light beam path;

d. means for intermittently moving said holding means in one direction across first and second portions of the light path at the same time, said moving means producing alternately at each resting state a first condition in which a new sample is in said first portion of the light path and a spaced portion of said holding means between two samples already exposed to said light beam in the first portion thereof is in said second portion, and a second condition in which a new portion of the holding means between two samples is in said first portion and a sample already exposed to said light beam in the first portion thereof is in said second portion.

each sample exposed to the light beam in said first portion becoming exposed to the beam in said second portion after lapse of a constant time interval, e. means for detecting alternately at each resting state a first signal corresponding to the light absorbance of each sample when said each sample and spaced portion are exposed to said first light beam, and a second signal corresponding to the light absorbance when said each sample and each spaced portion are exposed to said second light beam, f. a first signal subtraction device connected with said detecting means to produce a differential signal between said each first and second signals at each resting state;

g. a signal memory device connected to said first subtraction device to memorize first differential signals which are produced from said subtraction device in said first condition, said memory device being capable of storing a given number of the first differential signals in sequence and for successively reading out the earliest applied signal as each new signal is applied thereto, and h. a second subtraction device connected with the first subtraction device to receive second differential signals which are produced from said first subtraction device in said second condition and connected with said memory to produce a differential signal between each first differential signal and each second differential signal corresponding to the change in light absorbance of each sample at said time interval.

2. Apparatus according to claim 1, wherein said sample holding means holds said samples in a linear line and is movable linearly and said directing means includes reflecting means which directs said light beam along a line across said first and second portions of the light path.

3. Apparatus according to claim 1, wherein said light beam path is linear and said sample holding means is movable along a non-linear path between said two portions of said light beam path.

4. Apparatus according to claim 2, further comprising means operative to identify a non-linear condition of said reaction velocity at said time interval.

5. Apparatus according to claim 1, further comprising means operative to identify a non-linear condition of said reaction velocity at said time interval.

6. Apparatus according to claim 5, wherein said means operative to identify said non-linear condition include a circuit operative in response to said light absorbance measurements taken at said first and second portions to produce control signals corresponding to the rates of change of light absorbance of said reaction velocity at each of said first and second portions, a subtractor for obtaining the difference of said two control signals, and means operative to produce an abnormality signal in response to the output of said subtractor when such output exceeds a predetermined standard level.

7. Apparatus according to claim 6, wherein said circuit to produce control signals is a differentiating circuit.

8. Apparatus according to claim 6, wherein said circuit to produce control signals is an integrating circuit.

9. A method for measuring the velocity of a chemical reaction by detecting the changes in light absorbance of samples in which said reaction is taking place, said method comprising:

generating a first light beam of a wavelength ($\lambda_1$) and a second light beam of a wavelength ($\lambda_2$) alternately;

holding said samples in a line so that each sample is spaced by a predetermined distance;

directing said two light beams along one light beam path;

moving said holding means intermittently in one direction across a first portion and a second portion of the light at the same time so that a first condition in which a new sample is in said first portion and a spaced portion of said holding means between two samples which is already exposed to said light beam in the first portion is in said second portion and a second condition in which a new spaced portion of the holding means between two samples is in said first portion and a sample already exposed to said light beam in the first portion is in said second portion are produced alterately at each resting state and so that each sample exposed to the light beam in said first portion becomes exposed to the beam in said second portion after lapse of a constant time interval;

detecting alternately at each resting state a first signal corresponding to the total light absorbance of each sample and each spaced portion when said each sample and space portion are exposed to said first light beam and a second signal corresponding to said total light absorbance when said each sample and each space portion are exposed to said second light beam;

producing a first differential signal between said each first and second signals in said first condition and a second differential signal between said each first and second signals in said second condition, respectively at each resting state of said intermittent movement;

memorizing a given number of said first differential signals in sequence and for successively reading out the earliest applied first differential signal as each new first differential signal is applied thereto; and producing a differential signal between each first differential signal and each second differential signal corresponding to the change in light absorbance of each sample at said time interval.

10. The method according to claim 9, further comprising the step of determining a non-linear condition of said reaction velocity at said time interval.

* * * * *

UNITED STATES PATENT AND TRADEMARK OFFICE
CERTIFICATE OF CORRECTION

PATENT NO. : 4,063,816
DATED : December 20, 1977
INVENTOR(S) : NOBUO ITOI, et al.

It is certified that error appears in the above-identified patent and that said Letters Patent are hereby corrected as shown below:

Column 7, line 17, change "X, Y" to -- X, X' --.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks